United States Patent
Kelly

(10) Patent No.: US 7,297,827 B2
(45) Date of Patent: Nov. 20, 2007

(54) USE OF MONOLITH CATALYST TO PREPARE ETHYLBENZENE

(75) Inventor: Kevin Kelly, Friendswood, TX (US)

(73) Assignee: Fina Technology, Inc., Houston, TX (US)

( * ) Notice: Subject to any disclaimer, the term of this patent is extended or adjusted under 35 U.S.C. 154(b) by 129 days.

(21) Appl. No.: 10/998,415

(22) Filed: Nov. 29, 2004

(65) Prior Publication Data

US 2006/0116539 A1 Jun. 1, 2006

(51) Int. Cl.
- *C07C 2/66* (2006.01)
- *C07C 2/70* (2006.01)
- *C07C 2/68* (2006.01)

(52) U.S. Cl. .................. 585/467; 585/458; 585/459; 585/462; 585/466

(58) Field of Classification Search .......... 585/467, 585/458, 459, 462, 466
See application file for complete search history.

(56) References Cited

U.S. PATENT DOCUMENTS

| | | | | |
|---|---|---|---|---|
| 4,721,826 | A * | 1/1988 | Tiltscher et al. | 585/467 |
| 5,081,323 | A * | 1/1992 | Innes et al. | 585/449 |
| 5,304,698 | A | 4/1994 | Husain | 585/722 |
| 5,744,673 | A | 4/1998 | Skeels et al. | 585/474 |
| 6,376,730 | B1 | 4/2002 | Jan et al. | 585/467 |
| 6,759,358 | B2 | 7/2004 | Huang et al. | 502/64 |
| 6,762,149 | B2 | 7/2004 | Tonkovich et al. | 502/439 |
| 6,780,805 | B2 | 8/2004 | Faber et al. | 502/66 |
| 6,787,023 | B1 | 9/2004 | Mohr et al. | 208/27 |
| 6,797,247 | B2 | 9/2004 | Becue et al. | 423/239.1 |
| 6,803,015 | B2 | 10/2004 | Vance et al. | 264/628 |

FOREIGN PATENT DOCUMENTS

| | | |
|---|---|---|
| EP | 0987237 B1 | 11/2003 |
| WO | WO91/16285 | 10/1991 |

OTHER PUBLICATIONS

F. Camacho et al., *Alkylation of Benzene with Ethylene Using $AlCl_3$ as a Catalyst*, Institution of Chemical Engineers, Chem Eng Res Des, vol. 64, Jul. 1986, pp. 273-278.

Giuseppe Gozzelino et al.; *Gationic Reactivity of Olefins Present in the C5 Fraction*, Ind Eng. Chem. Res., vol. 42, No. 22, 2003, pp. 5437-5439.

Jacob A. Moulijn; *Structured Catalysts and Reactors: A Contribution to Process Intensification*, pp. 191-226, 25 Figs., 3 Tables, Jan. 2004 To Apr. 11, 2007.

* cited by examiner

*Primary Examiner*—Thuan Dinh Dang
(74) *Attorney, Agent, or Firm*—Madan, Mossman & Sriram, P.C.; Shirley A. Kopecky

(57) ABSTRACT

Disclosed is an alkylation reactor for preparing ethylbenzene. The reactor comprises a monolith catalyst system that includes a monolith support impregnated or co-formed with a catalyst suitable to catalyze the alkylation of benzene with ethylene. The catalyst may be selected from, for example, zeolites such as beta zeolite and MCM-22 zeolite, and fixed super acids. Also disclosed is a method of preparing ethylbenzene by alkylating a mixture of benzene and ethylene in an alkylation reactor comprising a monolith catalyst system, including a monolith support impregnated or co-formed with a suitable catalyst. In one embodiment the invention provides a convenient means of upgrading an existing reactor that has previously been used for conventional liquid phase alkylations such as those catalyzed by aluminum trichloride. The inventive alkylation method may be effectively and advantageously carried out under critical or near critical conditions, if desired.

16 Claims, No Drawings

USE OF MONOLITH CATALYST TO PREPARE ETHYLBENZENE

BACKGROUND OF THE INVENTION

1. Field of the Invention

The present invention relates to alkylation reactions to prepare ethylbenzene. More particularly, the invention relates to a catalyst and reactor system to prepare ethylbenzene.

2. Background of the Art

Ethylbenzene is an important product with a variety of uses including, in particular, as a precursor for styrene production. While a wide variety of preparation routes may be employed, one commonly employed method is a simple liquid phase alkylation of benzene with ethylene that is usually promoted with conventional acidic catalysts, such as Friedel-Crafts type catalysts, and in particular with aluminum trichloride catalyst. Because this method has been known for many years, many commercial production facilities have been designed toward its use. Thus, this method is still used to prepare billions of pounds of ethylbenzene every year.

Unfortunately, aluminum trichloride is an extremely corrosive material. Thus, its use presents very significant safety and environmental problems. It must be handled very carefully and, like most catalysts, it is typically recycled to improve production economics. Even with recycle, however, a proportion is always lost in the hydrocarbon product and must then be neutralized with caustic and, ultimately, removed, thus presenting a waste problem. Finally, because of its extreme corrosivity, its use is restricted to reactors made of special alloys. These reactors typically cost several times more than conventional stainless steel reactors of equivalent dimensions.

Alkylation may also be performed in a multiple fixed bed reactor system.

These fixed bed designs have been found to be useful for alternative liquid and gas phase methods for preparing ethylbenzene. The fixed beds frequently include supported catalysts. However, because of the limited solubility of ethylene in benzene, many fixed beds are needed to ensure an overall low ratio of benzene to ethylene.

It would therefore be desirable in the art to provide a method and means of preparing ethylbenzene that avoids use of corrosive or otherwise dangerous catalysts such as aluminum trichloride, and that may be used in the existing alkylation reactor units including those that have historically been used for conventional Friedel-Crafts type alkylations of benzene with ethylene. It would also be desirable for such alkylation to be able to be carried out at relatively low benzene to ethylene ratios.

SUMMARY OF THE INVENTION

In one aspect the invention is an alkylation reactor for preparing ethylbenzene. The reactor comprises a monolith catalyst system. The monolith catalyst system includes a monolith support impregnated or co-formed with any catalyst capable of catalyzing the alkylation of benzene with ethylene to produce ethylbenzene. Such catalyst may be, for example, selected from the group consisting of zeolites, including for example beta zeolite and MCM-22 zeolite, and fixed super acids.

In another aspect, the invention is a method of preparing ethylbenzene by alkylating a mixture of benzene and ethylene in an alkylation reactor comprising such monolith catalyst system, to produce ethylbenzene.

DETAILED DESCRIPTION OF INVENTION

The invention provides an alkylation reactor and a method of preparing ethylbenzene using the reactor. In one embodiment it represents a way to upgrade or retrofit an existing alkylation reactor at relatively low cost and with production improvements. In another embodiment the method offers improvements in a process using either a new or retrofitted reactor. These improvements may include the potential of running the process under critical or near-critical liquid reaction conditions. The method may therefore offer relatively low processing costs and reduced production of undesirable non-ethylbenzene phases.

In one embodiment the invention is a reactor that may be used for efficient alkylation of benzene with ethylene to produce ethylbenzene. This alkylation is promoted by a monolith catalyst system. The monolith catalyst is desirably disposed within the reactor in a location and at an orientation such that flow through it may be optimized. The product of the reaction is then flowed out of the reactor for further processing as desired. To facilitate the flow, and particularly counter-current flow (internal recycle), of the reactants, it may be desirable in some embodiments to include within the reactor flow facilitators such as impellers, injection means, pressure means, spray means, combinations thereof, and the like. A particular advantage of the inventive reactor is that typical commercial vessels, already being used for alkylation with conventional catalysts such as aluminum trichloride, may be easily and relatively inexpensively refitted with the described monolith catalyst to prepare the inventive alkylation reactor.

In general monolith catalyst systems are defined as systems comprising a porous, inorganic structure, frequently a sintered ceramic, which is the monolith support, which serves as a substrate for a catalyst that is applied thereto as an impregnant. In some embodiments catalysts may also or alternatively be incorporated within the inorganic matrix in conjunction with formation of the structure ("co-formed"), such as via co-extrusion or other means of co-formation, and the structure may then be sintered or otherwise processed. The porous inorganic may be prepared as a foam (a solid structure that upon micro examination is predominantly cellular space), felt (a non-woven structure wherein fiber-like structures are oriented in one or more specific directions), wad (a non-woven tangle of non-oriented fiber-like structures), honeycomb (a predominantly solid matrix containing both larger channels and pores), or combination thereof. Where it is a honeycomb, it may frequently be prepared by extrusion.

Regardless of structure, however, it is desirable that the monolith support have a relatively high pore density and walls that are as thin as possible but which enable the monolith catalyst system to withstand the rigors of the alkylation reactions it will undergo. Routine engineering design and modeling may be used to select particularly desirable configurations, but any type of structure known in the art may be employed herein.

In configuration the monolith catalyst system may be shaped in any way that does not interfere with, and desirably facilitates, flow of the reactants. One particularly effective shape is a "donut", with current flow occurring along its outside edges and counter-current, or recycle, flow occurring through the middle "hole".

To prepare the monolith catalyst system a suitable monolith support material may be selected. This material may be any which is capable of withstanding the reaction temperatures and pressures, and which is inert to the selected catalyst. Frequently suitable choices include, for example, cordierite, which is a magnesium aluminum silicate; other silicon-based materials such as silicon carbide and silicon nitride as well as silica-thorias and silica-alumina-thorias; mullite; beta spodumene; aluminas such as alpha and theta alumina; magnesia; metals; phosphate ceramics such as zirconium phosphate; titanias such as alumina-titanias; combinations thereof; and the like. In one embodiment a cordierite monolith support may be selected. The monolith catalyst material may also be a composite material, or one into which a catalyst is incorporated during the construction thereof. Those skilled in the art will be familiar with such compositions, such as are disclosed in, for example, U.S. Pat. Nos. 6,787,023 and 6,780,805, the disclosures of are incorporated herein by reference.

In one embodiment one or more desired reactants are passed through the inorganic structure wherein they contact the catalyst, with the result that the desired reaction is effectively catalyzed and thereby facilitated. Selection of a suitable catalyst may be made from among any catalysts that are capable of catalyzing the alkylation of benzene with ethylene. Such catalysts are desirably further capable of impregnating or being co-formed with a given selected monolith support. Impregnation as used herein refers to the significant absorption and retention, within the ceramic's pores, of the catalyst, the catalyst therefore being in a liquid, slurry or gaseous form prior to absorption. Such absorption is furthermore preferably such that the catalyst does not occlude the pores in such a way that the reactants, e.g., benzene and ethylene, are not able to efficiently flow therethrough. In supplemental or alternative embodiments, co-forming refers to incorporation of the catalyst within and throughout the inorganic matrix in conjunction with formation of the structure, by means such as co-extrusion. In either case the adherence of the catalyst to the inorganic monolith support may be facilitated by use of conventional binders, or the catalyst and monolith support materials may be selected to obtain suitable adhesion or cohesion between them. Those skilled in the art will be familiar with ways to ensure desirable retention of the catalyst on and within and/or throughout the monolith support, such as that described in, for example, U.S. Pat. No. 6,762,149, the disclosure of which is incorporated herein by reference.

In general, a wide selection of catalysts already known to be useful for the alkylation of benzene with ethylene in fixed bed reactors may be employed herein. A suitable catalyst may be selected from, for example, beta zeolites, the MCM-22 zeolite (available from EXXONMOBIL™), super acid catalysts, combinations thereof, and the like. Zeolites in general may be desirably selected. These are a discrete group of molecular sieves that are structured as a lattice of silica and optionally alumina, with exchangeable cations such as alkali or alkaline earth metal ions. As the term "zeolites" is used herein, also included among possible selections are technically related materials, which are similar to zeolites but wherein the silica and alumina portions may be replaced in whole or in part with other oxides. A third group, also considered to be "zeolites" as the term is used herein, are the ALPO-based molecular sieves which contain framework tetrahedral units of alumina and phosphorus and, optionally, silica. In one embodiment beta zeolite may be desirably employed. In other embodiments Y-type zeolites may be employed. In general the H-form zeolites, including beta zeolite and MCM-22, for example, but also ZSM and mordenite zeolites, are desirably selected because of their proton-donating (Bronsted-Lowry acid) functionality.

Also desirably selected are fixed super acids. Fixed super acid catalysts may be selected from, for example, strong acids such as sulfur-based acids; any compounds acting as Bronsted-Lowry acids or Lewis acids; heteropoly acids; combinations thereof; and the like. Representative sulfur acid catalysts include the sulfonic acid catalysts, sulfated zirconia (commercially available, for example, from MEI Chemicals) and the perfluorinated ionic exchange polymers that are available from E.I. Dupont de Nemours, Inc. under the trademark NAFION. The latter type of material is described in U.S. Pat. No. 5,001,281, the disclosure of which is incorporated herein by reference. Heteropoly acid catalysts useful herein include those described in, for example, U.S. Pat. No. 5,300,703 of J. F. Knifton, the disclosure of which is incorporated herein by reference. Such acids may be "fixed" on and within the monolith support using any means known to those skilled in the art.

To prepare the monolith catalyst system methods generally known to those of ordinary skill in the art may be employed. One method is described in, for example, M. Ulla, et al., "Synthesis and Characterization of ZSM-5 Coatings onto Cordierite Honeycomb Supports", *Applied Catalysis* A: General 253 (2003) 257-269, the disclosure of which is incorporated herein by reference. Where an impregnation method is selected, any of the conventional impregnation methods, such as, for example, solution impregnation by the conventional dipping technique, may be employed. In other embodiments, co-extrusion and other co-formation techniques may be selected and are well-known to those skilled in the art. Further information on monolith catalyst preparation is available in "Structured Catalysts and Reactors", edited by A. Cybulski and J. A. Moulijn, Marcel Dekker Inc., publisher, 1998, the disclosure of which is incorporated herein by reference.

In one embodiment it may be desirable to include a so-called catalyst promoter with the catalyst being applied to or incorporated into the monolith support. Promoters operate as co-catalysts and, as such, enhance the overall catalytic activity of the selected catalyst without substantially increasing overall catalysis costs. Suitable promoters may be selected from a wide variety of metals, including rare earth metals such as cerium, yttrium, lanthanum, praseodymium, and neodymium; the alkaline-earth metals such as calcium, magnesium, barium and titanium; and mixtures thereof. One promoter that has been found to be particularly effective is cerium, and a particularly effective combination is the use of a cerium promoter with a beta zeolite catalyst. This catalyst/promoter combination may, in one embodiment, be used to impregnate a cordierite monolith support for use in the inventive alkylation reactor. In another embodiment the catalyst/promoter combination may be co-extruded with the cordierite or other monolith support material.

The inventive alkylation reactor may, in one embodiment, be used to carry out the alkylation of benzene with ethylene to prepare ethylbenzene. In general this method of preparing ethylbenzene involves routing the two reactants into a reactor vessel fitted with the monolith catalyst system described hereinabove, and flowed appropriately such that the reactants pass through the impregnated or co-formed monolith catalyst system. The resulting product, which is a mixture of ethylbenzene and so-called "heavies", is then removed from or flowed out of the reactor for the additional processing steps required to obtain a useful ethylbenzene fraction. These additional steps may in some embodiments include a transalkylation process, and also generally include at least one distillation carried out in a conventional distillation unit. A final benzene fraction is also generally produced, and this fraction may be recycled by mixing it with fresh benzene prior to introduction back into the alkylation reactor. In various inventive embodiments the benzene to ethylene molar ratio may be desirably maintained in a range from about 0.7:1 to about 25:1. Desirably, the ratio is kept relatively low, with commercial operations being desirably carried out at a ratio from about 0.7:1 to about 3.5:1. Thus, it is desirable to increase the ethylene feed rate appropriately to compensate for the recycled benzene.

Conditions of temperature and pressure under which the inventive alkylation method may be carried out include those typical of liquid phase reactions, but they may alternatively, and notably, be those suitable to define the alkylation as a critical or near critical process. Liquid phase alkylation may be accomplished at temperatures desirably ranging from about 100° C. to about 290° C. and pressures ranging from ambient to about 350 psig. These conditions are well below the critical temperature of benzene, which is the temperature above which benzene in gas phase cannot be liquefied no matter how great a pressure is applied (i.e., the highest temperature at which benzene can exist as a liquid), and the critical pressure of benzene, which is the minimum pressure required to bring about liquefaction at the critical temperature. While these true liquid phase conditions may be employed herein, a particular advantage of the invention is that, in some embodiments, the alkylation may alternatively be carried out at temperatures above the critical temperature of benzene ($T_c$=290° C.) where pressure is also greater than the critical pressure of benzene ($P_c$=714 psig, which is 48.6 atm), with the result that the reactants exhibit behaviors characteristic to both gases and liquids. This includes operation under critical and near critical conditions at temperatures ranging from about 200° C. to about 450° C., and pressures ranging from about 300 psig to about 1000 psig. As used herein, the term "near critical" refers to operation under a combination of temperature and pressure where the reactants exhibit behavior other than that characterized as true liquid behavior, but which conditions do not meet the definition of true critical conditions wherein temperature is greater than 290° C. and pressure is greater than 714 psig. Notably, a significant advantage seen under these near critical and, especially, critical conditions, as compared to conventional gas phase operation, is that production of "heavies" including, for example, 1,1-diphenylethane, is greatly reduced. Another advantage encountered in the invention's use of critical and near critical processing conditions, in some embodiments, is that the operation exhibits a selectivity similar to that attained in conventional liquid phase processing conditions.

EXAMPLES

The following hypothetical examples are provided for purposes of illustration. The examples are not intended to limit the invention's scope and should not be construed as such.

Hypothetical Example 1

In a 1-billion pound per year ethylbenzene plant the reactor is fitted with a monolith catalyst system prepared from a cordierite ($2MgO-2Al_2O_3-5SiO_2$) honeycomb monolith having 400 cells per square inch, and a 0.1 mm average wall thickness. The monolith density and its external specific area are 1554 kg/m$^3$ and 3650 m$^2$/m$^3$, respectively. The monolith is impregnated by wash-coating it with a slurry of beta zeolite/cerium, having an average particle size of 13 to 18 microns. The wash-coat loading of the monolith is about 14 percent by weight.

A heavies yield of about 0.35 percent by weight is assumed, and therefore for a 1-billion pound of ethylbenzene yield, the amount of ethylene feed needed is calculated as 265,075,000 pounds. The desired molar benzene to ethylene ratio is calculated to be close to 1.0. Therefore, and taking loss to heavies into account, a total of 738,425,000 pounds of benzene will be required.

Converting these figures to hourly feed rates, 30,260 pounds of ethylene and 84,295 pounds of benzene are fed into the reactor under critical conditions (inlet temperature of 290° C. and a pressure of 750 psig) to produce a product which is a mixture of 114,155 pounds of ethylbenzene and 400 pounds of heavies, as measured per hour. The molar ratio of benzene to ethylene is monitored and maintained by increasing ethylene feed as needed according to the amount of recycle benzene returned to the reactor. The heavies are then removed via successive distillations until a commercially acceptable ethylbenzene fraction is procured.

Hypothetical Example 2

The production of ethylbenzene is carried out using the equipment and feed rates and amounts of Example 1, but under liquid phase conditions wherein the inlet temperature is 220° C. and the pressure is 500 psig.

The description provided hereinabove is intended to generally describe the features and some useful embodiments of the invention. However, it will be appreciated that modifications may be made to many aspects of the invention without departing from its scope and generalized objects. For example, selection of temperatures, pressures, reactor vessel configurations, feed rates, specific catalysts, monolith supports, and the like, not explicitly listed but which do not substantially alter the outcome of the process or the character of the products will still fall within the scope of the invention.

What is claimed is:

1. A method of preparing ethylbenzene comprising:
providing a reactor having a flow facilitator comprised of an impeller for internally recycling reactants comprised of benzene and ethylene;
placing a monolith catalyst system within said reactor, wherein said system includes a monolith support impregnated or co-formed with a catalyst suitable to catalyze the alkylation of benzene with ethylene to produce ethylbenzene;
wherein the flow facilitator causes a flow along or through the monolith catalyst system; and
alkylating a mixture of benzene and ethylene within the reactor.

2. The method of claim 1 wherein the catalyst is selected from the group consisting of zeolites and fixed super acids.

3. The method of claim 2 wherein the zeolite is selected from the group consisting of beta zeolite and MCM-22 zeolite.

4. The method of claim 2 wherein the catalyst is a fixed super acid and is selected from the group consisting of Bronsted-Lowry acids, Lewis acids, heteropoly acids, and combinations thereof.

5. The method of claim 1 wherein the monolith support is selected from the group consisting of cordierite, silicon carbide, silicon nitride, silica-thorias, silica-alumina-thorias, mullite, beta spodumene, aluminas, magnesia, metals, zirconium phosphate, alumina-titania, and combinations thereof.

6. The method of claim 1 wherein the monolith catalyst system further comprises a catalyst promoter.

7. The method of claim 6 wherein the catalyst promoter is selected from the group consisting of cerium, yttrium, lanthanum, praseodymium, neodymium, calcium, magnesium, barium, titanium, and mixtures thereof.

8. The method of claim 7 wherein the catalyst is beta zeolite and the catalyst promoter is cerium.

9. The method of claim 1 wherein the alkylation is carried out at a temperature from 100° C. to 450° C. and a pressure from ambient to 1000 psig.

10. The method of claim 9 wherein the alkylation is carried out under critical or near critical conditions at a temperature of from 200° C. to 450° C. and a pressure of from 300 psig to 1000 psig.

11. The method of claim 1 wherein the alkylation is carried out with benzene and ethylene in a molar ratio from 0.7:1 to 25:1.

12. The method of claim 1 wherein the alkylation is carried out with benzene and ethylene in a molar ratio from 0.7:1 to 3.5:1.

13. The method of claim 1 further comprising the step of using the flow facilitators and the monolith catalyst in a new reactor.

14. The method of claim 1 wherein the reactants are internally recycled through a hole in the monolith catalyst.

15. A method of preparing ethylbenzene comprising:

alkylating a mixture of benzene and ethylene in an alkylation reactor;

providing a flow facilitator comprised of an impeller for internally recycling the benzene and ethylene within the reactor;

wherein the reactor is further comprised of a monolith catalyst system including a monolith support impregnated or co-formed with a catalyst selected from the group consisting of zeolites and fixed super acids;

wherein the flow facilitator causes a flow along or through the monolith catalyst system; and wherein the alkylation of benzene with ethylene is carried out at a temperature from 100° C. to 450° C. and a pressure from ambient to 1000 psig.

16. The method of claim 15 wherein the alkylation is carried out under critical or near critical conditions at a temperature of from 200° C. to 450° C. and a pressure of from 300 psig to 1000 psig.

* * * * *